(12) United States Patent
Adolf et al.

(10) Patent No.: US 9,274,120 B2
(45) Date of Patent: Mar. 1, 2016

(54) STRATIFICATION OF PANCREATIC AND OVARIAN CANCER PATIENTS FOR SUSCEPTIBILITY TO THERAPY WITH PTK2 INHIBITORS

(71) Applicants: Guenther Adolf, Vienna (AT); Pilar Garin-Chesa, Vienna (AT); Ulrich Hirt, Ummendorf (AT)

(72) Inventors: Guenther Adolf, Vienna (AT); Pilar Garin-Chesa, Vienna (AT); Ulrich Hirt, Ummendorf (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/221,370

(22) Filed: Mar. 21, 2014

(65) Prior Publication Data
US 2014/0205592 A1    Jul. 24, 2014

Related U.S. Application Data

(63) Continuation of application No. 13/237,833, filed on Sep. 20, 2011, now abandoned.

(30) Foreign Application Priority Data

Sep. 28, 2010 (EP) ..................... 10180981

(51) Int. Cl.
| | | |
|---|---|---|
| *G01N 33/53* | (2006.01) | |
| *C12Q 1/00* | (2006.01) | |
| *G01N 33/574* | (2006.01) | |
| *C12Q 1/68* | (2006.01) | |

(52) U.S. Cl.
CPC ........ *G01N 33/57492* (2013.01); *C12Q 1/6886* (2013.01); *G01N 33/57484* (2013.01); *G01N 33/57496* (2013.01); *G01N 2333/705* (2013.01); *G01N 2333/91205* (2013.01); *G01N 2800/52* (2013.01)

(58) Field of Classification Search
None
See application file for complete search history.

(56) References Cited

U.S. PATENT DOCUMENTS

| 8,445,211 | B2 | 5/2013 | Arpin et al. |
|---|---|---|---|
| 2009/0092596 | A1 | 4/2009 | Haley et al. |
| 2010/0317000 | A1 | 12/2010 | Zhu |

FOREIGN PATENT DOCUMENTS

| CN | 1554025 A | 12/2004 |
|---|---|---|
| FR | 2919061 A1 | 1/2009 |
| WO | 02073204 A2 | 9/2002 |
| WO | 2008115443 A1 | 9/2008 |
| WO | 2009012708 A1 | 1/2009 |
| WO | 2009105498 A1 | 8/2009 |

OTHER PUBLICATIONS

Alt-Holland et al., E-cadherin suppression is coordinates with elevated FAK expression and redistribution leading to a highly motile, invasive phenotype, J. Investig. Dermatol. 126, S1, 2006.
(Continued)

*Primary Examiner* — Elly-Gerald Stoica
(74) *Attorney, Agent, or Firm* — Michael P. Morris; Alan R. Stempel

(57) ABSTRACT

The present invention relates to a method for determining whether a cancer patient is susceptible to treatment with a protein tyrosine kinase 2 (PTK2) inhibitor, comprising detecting the expression of the E-cadherin protein in a cancer sample of said cancer patient, wherein an E-cadherin protein immunoreactivity score (IRS) of 0-2 indicates that the cancer patient is susceptible to treatment with a PTK2 inhibitor. Said detection of the expression of the E-cadherin protein in a cancer sample of a cancer patient is preferably conducted by way of an immunohistochemistry (IHC) method. Said IHC method preferably employs a primary antibody which is specific for E-cadherin and a secondary antibody which specifically reacts with the primary antibody. The present invention also relates to a method of treating a cancer patient whose cancer is characterized by an E-cadherin protein immunoreactivity score (IRS) of 0-2, comprising administering to the patient a therapeutically effective amount of a PTK2 inhibitor. In a further aspect, the present invention relates to a PTK2 inhibitor for use in the treatment of a cancer patient whose cancer is characterized by an E-cadherin protein immunoreactivity score (IRS) of 0-2. The present invention also provides a method of screening for a therapeutically effective PTK2 inhibitor comprising the steps of (a) providing cancer cells or a cancer cell line which are characterized by an E-cadherin protein immunoreactivity score of 2, 1, or 0 (1 being preferred and 0 being even more preferred); (b) contacting the cancer cell or the cancer cell line of (a) with a PTK2 inhibitor; and (c) evaluating whether the PTK2 inhibitor negatively affects the cancer cell/cancer cell lines. In a further aspect, the present invention relates to a method for stratifying cancer patients that are susceptible to treatment with a PTK2 inhibitor, comprising determining the E-cadherin IRS score in a cancer sample of said patient, wherein an E-cadherin protein immunoreactivity score (IRS) of 0-2 (i.e. 2, 1, or 0) indicates that the cancer patient is susceptible to treatment with a PTK2 inhibitor. The present invention also relates to a pharmaceutical package comprising a PTK2 inhibitor, and (a) instructions and/or an imprint indicating that said PTK2 inhibitor is to be used for the treatment of patients which suffer from a cancer which is characterized by an E-cadherin protein immunoreactivity score of 2, 1, or 0 (1 being preferred and 0 being more preferred); and/or (b) instructions and/or an imprint indicating that said patient is to be stratified by a method of the present invention; and/or (c) means to carry out a method as defined herein.

5 Claims, 2 Drawing Sheets

(56) References Cited

OTHER PUBLICATIONS

Alt-Holland et al., Silencing of FAK and Src kinases normalizes human, 30 tissue models of squamous cell carcinoma harboring E-cadherin- deficient tumor cells, J. Investig. Dermatol. 129, S31, 2009.

International Search Report, form PCT/ISA/210, for corresponding application PCT/EP2011/066636, date of mailing Oct. 31, 2011.

Rodrigo et al., Focal Adhesion Kinase and ECadherin as Markers for Nodal Metastasis in Laryngeal Cancer, Arch. Otolaryngol.Head Neck Surg. 133, 145-150, 2007.

Saito et al., Hypermethylation in Promoter Region of E-cadherin Gene Is Associated with Tumor Dedifferention and Myometrial Invasion in Endometrial Carcinoma, Cancer, 2003, vol. 97, 4.

Sawada et al., Loss of E-Cadherin Promotes Ovarian Cancer Metastasis via a5-Integrin, which Is a Therapeutic Target, Ca. Res. 68, 2329-2339,2008.

Schwock et al. SNAI1 expression and the mesenchymal phenotype: an immunohistochemical study performed on 46 cases of oral squamous cell carcinoma BMC Clinical Pathology 10, 1, 2010.

Smit et al. Osteonectin down regulates E-cadherin, induces Osteopontin and Focal adhesion kinase activity stimulating an invasive melanoma phenotype, Int. J. of Cancer, 121, 2653-2660, 2007.

Wang et al., Expression of ezrin, E-cadherin and focal adhesion kinase in colorectal carcinoma and their clinical significances, Shijie Huaren Xiaohua Zazhi, 15, 591-595, 2007—abstract only.

Wang et al., Significance of expression of E-cadherin and FAK in hepatocellular carcinoma, Zhonghua Zhongliu Fangzhi Zazhi 13, 926-928, 2006—abstract only.

Yin et al., Expressions and significances of E-cadherin and FAK in human astrocytoma, Linchuang Yixue 29, 94-96, 2009—abstract only.

Zhang et al., Significance and expression of E-cadherin and focal adhesion kinase in rectal cancer, Zhonghua Xiaohua Waike Zazhi, 9, 143-146, 2010—abstract only.

Zhao et al., Signal transduction by focal adhesion kinase in cancer, Cancer and Metsstasis Reviews, 28, 1-2, pp. 35-49, 2009.

E-cadherin expression

STRATIFICATION OF PANCREATIC AND OVARIAN CANCER PATIENTS FOR SUSCEPTIBILITY TO THERAPY WITH PTK2 INHIBITORS

The present invention relates to a method for determining whether a cancer patient is susceptible to treatment with a protein tyrosine kinase 2 (PTK2) inhibitor, comprising detecting the expression of the E-cadherin protein in a cancer sample of said cancer patient, wherein an E-cadherin protein immunoreactivity score (IRS) of 0-2 indicates that the cancer patient is susceptible to treatment with a PTK2 inhibitor. Said detection of the expression of the E-cadherin protein in a cancer sample of a cancer patient is preferably conducted by way of an immunohistochemistry (IHC) method. Said IHC method preferably employs a primary antibody which is specific for E-cadherin and a secondary antibody which specifically reacts with the primary antibody. The present invention also relates to a method of treating a cancer patient whose cancer is characterized by an E-cadherin protein immunoreactivity score (IRS) of 0-2, comprising administering to the patient a therapeutically effective amount of a PTK2 inhibitor. In a further aspect, the present invention relates to a PTK2 inhibitor for use in the treatment of a cancer patient whose cancer is characterized by an E-cadherin protein immunoreactivity score (IRS) of 0-2. The present invention also provides a method of screening for a therapeutically effective PTK2 inhibitor comprising the steps of (a) providing cancer cells or a cancer cell line which are characterized by an E-cadherin protein immunoreactivity score of 2, 1, or 0 (1 being preferred and 0 being even more preferred); (b) contacting the cancer cell or the cancer cell line of (a) with a PTK2 inhibitor; and (c) evaluating whether the PTK2 inhibitor negatively affects the cancer cell/cancer cell lines. In a further aspect, the present invention relates to a method for stratifying cancer patients that are susceptible to treatment with a PTK2 inhibitor, comprising determining the E-cadherin IRS score in a cancer sample of said patient, wherein an E-cadherin protein immunoreactivity score (IRS) of 0-2 (i.e. 2, 1, or 0) indicates that the cancer patient is susceptible to treatment with a PTK2 inhibitor. The present invention also relates to a pharmaceutical package comprising a PTK2 inhibitor, and (a) instructions and/or an imprint indicating that said PTK2 inhibitor is to be used for the treatment of patients which suffer from a cancer which is characterized by an E-cadherin protein immunoreactivity score of 2, 1, or 0 (1 being preferred and 0 being more preferred); and/or (b) instructions and/or an imprint indicating that said patient is to be stratified by a method of the present invention; and/or (c) means to carry out a method as defined herein.

Protein tyrosine kinase 2 (PTK2), also known as focal adhesion kinase 1 (FAK1) is a non-receptor tyrosine kinase that is predominantly localized in focal adhesions. PTK2 serves as a linker between extracellular signals transmitted through integrins and growth factor receptors and signal transducers inside the cells. Activated PTK2 appears to be involved in the regulation of cell survival, proliferation and motility. Therefore, inhibition of PTK2 may inhibit cancer growth and the formation of metastases. PTK2 inhibitors have been previously described and several compounds are currently under investigation in early clinical trials.

PTK2 kinase inhibitors show efficacy in a variety of experimental models of cancer, in particular in human cancer xenograft models in immunodeficient mice. However, their efficacy varies widely among different cancer models: whereas cancer regression or complete inhibition of growth can be achieved in some models, treatment of other cancer types results in partial inhibition of growth and some cancers are not affected at all. Oncogenic mutations or gene amplifications have been described for a number of genes, e.g. EGFR, HER2 or BRAF. Their presence determines the sensitivity of a given cancer to treatment with the corresponding kinase inhibitors, and eligibility of patients for therapy with such inhibitors can easily be determined by analysis of the cancer DNA sequence or gene copy number. For the PTK2 gene, however, no mutations or amplifications have been described so far in human cancers, or in the preclinical model tumors that are sensitive to PTK2 inhibition.

Therefore, the identification of predictive biomarkers for selection of patients most likely to benefit from therapy with PTK2 inhibitors is urgently required. No such predictive biomarkers or a genetic signature associated with therapeutic benefit are currently available.

Thus, the technical problem underlying the present invention is to provide means and methods for selecting susceptible cancer patients and/or cancer types for the treatment with PTK2 inhibitors.

The present invention addresses this need and provides the cellular markers and methods which will allow the selection of cancer patients susceptible to treatment with PTK2 inhibitors.

In our pre-clinical studies using xenograft models of human cancers, we have found surprisingly that the expression level of E-cadherin protein in cancer cells, which can be evaluated for example with immunohistochemistry (IHC) methods, can be used to predict sensitivity to PTK2 inhibitors. In view of that, we propose to examine the E-cadherin expression level prior to the administration of PTK2 inhibitors in order to determine whether a cancer/cancer patient is susceptible to treatment with a PTK2 inhibitor or not. Further embodiments of the present invention are characterized and described herein and also reflected in the claims.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein. Unless otherwise indicated, the term "at least" preceding a series of elements is to be understood to refer to every element in the series. "At least one" includes for example, one, two, three, four, or five or even more.

Those skilled in the art will recognize, or be able to ascertain using no more than routine experimentation, many equivalents to the specific embodiments of the invention described herein. Such equivalents are intended to be encompassed by the present invention. Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In a first aspect, the present invention relates to a method for determining whether a cancer and the respective cancer patient is susceptible to treatment with a protein tyrosine kinase 2 (PTK2) inhibitor, comprising detecting the expression of the E-cadherin protein in a cancer sample (obtained) from said cancer or cancer patient, wherein an E-cadherin protein immunoreactivity score (IRS) 0-2, preferably of 0-1, more preferably an IRS score of 1 and even more preferably an IRS score of 0, indicates that the cancer and the respective cancer patient is susceptible to treatment with a PTK2 inhibitor.

An IRS score (or IRS) of "0-2" means an IRS of 0, 1, or 2. Likewise, an IRS score of "0-1" means an IRS score of 0 or 1. Methods allowing the skilled person to evaluate said IRS score in a given cancer/cancer sample are explained herein elsewhere. The term "IRS" as used herein denotes the immunoreactivity score of E-cadherin as disclosed herein.

In a preferred embodiment, said detection is carried out by way of an immunohistochemistry method (IHC).

It will be understood that the cancer sample is preferably obtained from a cancer patient which, however, does not mean that the step of obtaining said cancer sample from said patient is necessarily included in the scope of the present invention.

"E-cadherin" or "E-cadherin protein", also known as CD324, LCAM or ECAD belongs to the "cadherins" (calcium-dependent adhesion molecules) which are a class of type-1 transmembrane proteins. They play important roles in cell adhesion, ensuring that cells within tissues are bound together. Cadherins are dependent on calcium ($Ca^{2+}$) ions to function, hence their name. The E-cadherin protein, encoded by the CDH1 gene, is composed of five extracellular cadherin repeats, a transmembrane region, and a highly conserved cytoplasmic tail and can be found in all epithelial tissues. The cytoplasmatic domain is bound to the actin cytoskeleton via intracellular attachment proteins, the catenins. The actin cytoskeleton forms a transcellular network that mediates the structural integrity of the cells and its polarity and is important for epithelial cell morphogenesis.

E-cadherin thus serves as a biomarker for epithelial cells and most epithelial-derived cancers. Recent immunohistochemical analyses have indicated that decreased membrane expression of E-cadherin on cancer cells is associated with adverse prognostic features and lower overall survival in patients with epithelial cancers (Saito T, et al; Cancer, 2003; 97:1002-9). It thus appears that E-cadherin is not only a biomarker for epithelial cells as such but may also serve as a prognostic marker for carcinoma progression.

The decreased protein expression or lack of expression of E-cadherin on the membrane of epithelial cancer cells was found in our preclinical studies to correlate, most to our surprise, as well with sensitivity of the respective cancer cells to PTK2 inhibition, translating into significant cancer growth inhibition and cancer regression in animal models of human cancer. Therefore, the E-cadherin expression level may serve as a biomarker for the selection of patients for treatment with PTK2 inhibitors. These PTK2 inhibitors are well-known to the skilled artisan and are also described in great detail herein below. It could be demonstrated by the present inventors that cancers with low E-cadherin expression, e.g. an E-cadherin score of 0-2, preferably of 0-1, more preferably an IRS score of 1 and even more preferably of 0 (said score being explained in detail herein), will more likely be susceptible to treatment with a PTK2 inhibitor than cancers with high E-cadherin expression.

The "membrane of the cancer cells" means the cell membrane which separates the exterior of a cancer cell from the interior of the cancer cell. E-cadherin is regularly expressed on the cell membrane of epithelial cells ensuring that cells within tissues are attached to each other to maintain tissue integrity.

The term "susceptible to treatment with a PTK2 inhibitor" when used herein means that a PTK2 inhibitor may potentially have a therapeutic effect in a patient to whom a PTK2 inhibitor is and/or will be administered. Said term when used herein is equivalent to the term "sensitive to treatment with a PTK2 inhibitor" or "responsive to treatment with a PTK2 inhibitor".

By "therapeutic effect" or "therapeutically effective" is meant that a PTK2 inhibitor may produce the therapeutic effect for which it is administered. Preferably, a therapeutic effect includes the reduction, stabilization or inhibition of progression of a cancer-associated symptom, such as cancer size, number of metastases or other symptoms which are caused by/associated with the presence and/or progression of a cancer. The response includes a complete response, a partial response, a stable disease (without progression or relapse), and/or a response with a later relapse of the patient. Preferably, as described herein the PTK2 inhibitor may affect that cancer cells will undergo cell death thereby, ameliorating and/or treating a cancer of a patient provided that said cancer cells express the PTK2 protein. The therapeutic effect of the respective methods or method steps of the present invention may be detectable by all established methods and approaches which will indicate a therapeutic effect. Alternatively, it is also envisaged that cancer markers in the serum of the patient (if present) are detected in order to diagnose whether or not the therapeutic approach is effective. The skilled person is aware of numerous other ways which will enable him or her to observe a therapeutic effect of a PTK2 inhibitor.

It is envisaged that a cancer sample of a patient who may be treated with a PTK2 inhibitor is to be obtained prior to the treatment, during the treatment and/or after the treatment with said PTK2 inhibitor. Preferably, the sample is obtained prior to the treatment in order to determine, in accordance with the means and methods of the present invention, whether or not a cancer patient may be susceptible to the treatment with a PTK2 inhibitor, whether or not a patient may respond favorably to the treatment with a PTK2 inhibitor, or whether or not a patient may benefit from the treatment with a PTK2 inhibitor.

The term "potentially" when used in the context of a therapeutic effect means that a PTK2 inhibitor—though such an inhibitor is deemed to have a therapeutic effect based on the outcome of the methods of the present invention—does not necessarily have to be therapeutically effective. This is so because—self-explanatory as it is—the methods of the present invention cannot provide a 100% safe prediction whether or not a patient may be susceptible to a PTK2 inhibitor, since, apart from the expression of the E-cadherin protein, individual factors such as age, body weight, general health, sex, diet, drug interaction and the like may have an influence as to whether or not a patient will be susceptible to a PTK2 inhibitor.

"Treat" or "treatment" as used herein, means to reduce, stabilize, or inhibit progression of a symptom, such as cancer size, number of metastases or other symptoms which are caused by/associated with the presence and/or progression of a cancer.

The term "cancer", as used herein, refers to malignant cell growth and proliferation, including all pre-cancerous and cancerous cells and tissues. Cancers are sometimes also denoted herein as malignant cancers or neoplasias or tumors. Invasive malignant cancers of transformed epithelial cells, i.e. carcinomas, are preferred in the embodiments of the present invention. It is therefore envisaged that, in the embodiments of the present invention, said cancer sample essentially consists of/comprises malignant epithelial cancer cells.

The cancers described herein may be metastatic (i.e. the cancer metastasizes) or non-metastatic.

It will be understood that a cancer to be treated with a PTK2 inhibitor in accordance with the embodiments of the present invention, expresses the PTK2 protein. As already discussed hereinbefore, the present invention relates in essence to a method for determining whether a cancer patient is susceptible to treatment with a PTK2 inhibitor. It goes without saying that the cancer patients to be treated are therefore patients with PTK2 polypeptide expressing cancer cells. A "PTK2 polypeptide-expressing cancer" is a cancer comprising cells that have a PTK2 polypeptide present. A "PTK2 polypeptide-expressing cancer" optionally produces sufficient levels of PTK2 polypeptide in cells thereof, such that a PTK2 inhibitor can interact with it. The PTK2 polypeptide may be determined in various ways, i.e. the skilled person is well aware how to test whether a cancer/cancer cell is PTK2-positive or not. It will be understood that the evaluation of the PTK2 polypeptide in the cancer cells is not mandatory, i.e. the embodiments of the present invention do not necessarily include this step. Presently, it is assumed that almost all relevant epithelial cancers express PTK2. Even so, and as mentioned before, the efficacy of PTK2 kinase inhibitors varies widely among different cancer models: whereas cancer regression or complete inhibition of growth can be achieved in some models, treatment of other cancer types results in partial inhibition of growth and some cancers are not affected at all. Thus, PTK2 expression as such is obviously not predictive for the susceptibility of a cancer to treatment with PTK-2 inhibitors. This gap has been closed by the present invention which provides, for the first time, a suitable biomarker which allows the identification of cancers/cancer patients which are susceptible to treatment with a PTK2-inhibitor: the mentioned biomarker is the E-cadherin expression as explained throughout the specification.

In the context of the present invention the term "cancer patient" (sometimes also denoted as "patient" or "subject") means a subject having a cancer described herein (including a subject diagnosed to suffer from a cancer) but also includes a subject during an adjuvant therapy, for example after the resection of the primary cancer.

Preferably, said subject is a mammalian, such as a human, a horse, a camel, a dog, a cat, a pig, a cow, a goat or a fowl. A human subject is most preferred. The compositions, compounds, uses and methods of the present invention are thus applicable to both human therapy and veterinary applications.

A "tissue sample" (sometimes also denoted as "cancer sample" or "sample of the cancer" or the like) is derived or obtained from a subject (the cancer patient) and may be obtained via biopsy such as needle biopsy, surgical biopsy, bone marrow biopsy etc. A cancer sample includes a specimen of a cancer, parts of a cancer, cancer cells derived from a cancer (including cancer cell lines which may be derived from a cancer and which are grown in cell culture) and also the cancer mass as a whole, but also cancer cell lines as such, and cells and/or tissue which are/is derived from a subject and which are/is suspected of being cancerous or which are/is suspected of comprising cancerous cells. It is thus envisaged that the cancer sample may also comprise non-cancerous cells. For example cancer cells and/or (micro) metastases are frequently surrounded by healthy, i.e. non-cancerous tissue, i.e. the cancer cells could then form a subset of cells within the healthy tissue. A cancer sample thereby could comprise a subset of healthy (non-cancerous) cells and a subset of cancerous cells. The term "sample" is interchangeable with "specimen".

A non-limiting exemplary list of cancers which can be treated with PTK2 inhibitors includes, but is not limited to, one or more of the following: intestinal cancer including carcinomas of the duodenum, colon, rectum, and anus; carcinoma of the pancreas (e.g. pancreatic adenocarcinoma); carcinoma of the bladder; lung tumours (small-cell lung cancer (SCLC), non-small-cell lung cancer (NSCLC) such as for example squamous cell carcinomas, adenocarcinomas (acinary, papillary, bronchiolo-alveolar) and large-cell bronchial carcinoma (giant cell carcinoma, clear-cell carcinoma); breast cancer such as ductal, lobular, mucinous or tubular carcinoma, Paget's carcinoma; uterine cancer (corpus carcinoma or endometrial carcinoma); CUP syndrome (Cancer of Unknown Primary); ovarian cancer (ovarian carcinoma—mucinous or serous cystoadenocarcinoma, endometrioid carcinomas, clear cell tumour, Brenner's tumour); gall bladder cancer; bile duct cancer such as for example Klatskin tumour; testicular cancer (germinal or non-germinal germ cell tumours); laryngeal cancer such as for example supra-glottal, glottal and subglottal tumours of the vocal cords; head and neck tumours (HNO tumours) such as for example tumours of the lips, and oral cavity (carcinoma of the lips, tongue, oral cavity), nasopharyngeal carcinoma (tumours of the nose, lymphoepithelioma), pharyngeal carcinoma, oropharyngeal carcinomas, carcinomas of the tonsils (tonsil malignoma) and (base of the) tongue, hypopharyngeal carcinoma, laryngeal carcinoma (cancer of the larynx), tumours of the paranasal sinuses and nasal cavity, tumours of the salivary glands and ears; eyelid tumours (basalioma or adenocarcinoma of the eyelid apparatus); liver cell carcinoma (hepatocellular carcinoma (HCC); stomach cancer (papillary, tubular or mucinous adenocarcinoma, adenosquamous, squamous or undifferentiated carcinoma; kidney cancer such as for example clear cell renal cell carcinoma, papillary renal cell carcinoma, chromophobe renal cell carcinoma and collecting duct carcinoma; oesophageal cancer; penile cancer; prostate cancer (e.g. hormone refractory prostate cancer); vaginal cancer or vaginal carcinoma; thyroid carcinomas such as for example papillary, follicular, medullary or anaplastic thyroid carcinoma; cancer of the urethra (carcinoma of the urethra, urothelial carcinoma) and cancer of the vulva.

Carcinoma of the duodenum, colon, rectum and anus; carcinoma of the pancreas (e.g. pancreatic adenocarcinoma); carcinoma of the urinary bladder; lung tumours (small-cell lung cancer (SCLC), non-small-cell lung cancer (NSCLC) such as for example squamous cell carcinomas, adenocarcinomas (acinary, paillary, bronchiolo-alveolar) and large-cell bronchial carcinoma (giant cell carcinoma, clear-cell carcinoma); breast cancer such as ductal, lobular, mucinous or tubular carcinoma, ovarian cancer (ovarian carcinoma—mucinous or serous cystoadenocarcinoma, endometriod carcinoma, and clear cell tumour); head and neck tumours; liver cell carcinoma (hepatocellular carcinoma (HCC); kidney cancer such as for example (clear cell renal cell carcinoma, papillary renal cell carcinoma, chromophobe renal cell carcinoma and collecting duct carcinoma); prostate cancer (e.g. hormone refractory prostate cancer); and cancer of the vulva, are of great importance and therefore preferred.

Protein tyrosine kinase 2 (PTK2), also known as FAK, FADK, FAK1, pp 125FAK, EC 2.7.10.2) is a cytoplasmic protein tyrosine kinase which is found concentrated in the focal adhesions that form at the cell membrane of cells growing in the presence of extracellular matrix constituents. The encoded protein is a member of the FAK subfamily of protein tyrosine kinases but lacks significant sequence similarity to kinases from other subfamilies. PTK2 has three functional domains: (1) a focal adhesion targeting (FAT) domain, which is important for localization of FAK to focal adhesions and for binding integrin-associated proteins such as paxillin and talin; (2) a catalytic domain with tyrosine kinase activity; and (3) a N-terminal domain, important for the interaction with integrins and growth factor receptors (Parsons, J. T. (2003). Focal adhesion kinase: The first ten years. J. Cell Sci. 116, 1409-1416). PTK2 has multiple phosphorylation sites that are required for binding to adaptor proteins containing SH2 domains. An important phosphorylation site is Tyr397, which appears to be important for the interaction of PTK2 with downstream signaling molecules such as Rho kinase.

Convincing evidence suggests that PTK2 plays an essential role in cell-matrix signal transduction pathways (Clark and Brugge 1995, Science 268: 233-239) and its aberrant activation is associated with an increase in the metastatic potential of cancers (Owens et al. 1995, Cancer Research 55: 2752-2755). PTK2 was originally identified as a 125 kDa protein highly tyrosine-phosphorylated in cells transformed by v-Src. PTK2 was subsequently found to be a tyrosine kinase that localizes to focal adhesions, which are contact points between cultured cells and their underlying substratum and sites of intense tyrosine phosphorylation. PTK2 is phosphorylated and, thus, activated in response to extracellular matrix (ECM)-binding to integrins. Recently, studies have demonstrated that an increase in PTK2 mRNA levels is accompanied by a more invasive behaviour of cancers and attenuation of the expression of PTK2 (through the use of antisense oligonucleotides) induces apoptosis in cancer cells (Xu et al. 1996, Cell Growth and Diff. 7: 413-418). In addition to being expressed in most tissue types, PTK2 is found at elevated levels in most human cancers, particularly in highly invasive and metastatic cancers. Even so, and as mentioned before, the efficacy of PTK2 kinase inhibitors varies widely among different cancer models. Thus, PTK2 expression as such is obviously not predictive for the susceptibility of a cancer to treatment with PTK-2 inhibitors. This gap has been closed by the present invention which provides, for the first time, a suitable biomarker which allows the identification of cancers/cancer patients which are susceptible to treatment with a PTK2-inhibitor: the mentioned biomarker is the E-cadherin expression as explained throughout the specification.

The term "PTK2 inhibitor" defines in the context of the present invention a compound or a plurality of compounds which interact(s) with PTK2 (preferably the human PTK2) such that the kinase activity is reduced. Assays which are suitable to detect such inhibitors are explained in more detail herein below. The term "plurality of compounds" is to be understood as a plurality of substances which may or may not be identical. The plurality of compounds may preferably act additively or synergistically. Said compound or plurality of compounds may be chemically synthesized or microbiologically produced and/or comprised in, for example, samples, e.g., cell extracts from, e.g., plants, animals or microorganisms.

The term "reduced PTK2 kinase activity" or "reducing the PTK2 kinase activity" as used herein defines the reduction of the kinase activity of PTK2, preferably to at least about the same level as compared to a normal/natural state of a comparable control-cell/subject. In this context, the term "normal/natural state of a comparable control-cell/subject" means the PTK2 kinase activity in a control-cell which is preferably of the same nature as the test-cell (e.g. both cells are epithelial cells) but which is derived from a different source. "A different source" includes e.g. a cell/tissue sample obtained from a healthy subject, preferably from a subject who does not suffer from a carcinoma or a cell/tissue sample obtained from a distinct part of the same subject wherein said distinct part appears to be free from associated symptoms of a carcinoma. However, even in cases where the PTK2 inhibitor will not reduce the kinase activity of PTK2 to about the normal/natural state of a comparable control-cell/subject but actually reduces the PTK2 kinase activity when compared to the PTK2 kinase activity before the addition of said inhibitor, it will be appreciated that said inhibitor has a beneficial effect.

Accordingly, it is envisaged that a PTK2 inhibitor at least reduces the kinase activity of PTK2 about 5%, 10%, 20%, 30%, 40%, 50%, 60%, 70%, 80%, 90% or even 100% when compared to the PTK2 kinase activity that is achieved without the addition of said inhibitor. Suitable test systems to measure the PTK2 kinase activity are disclosed herein. Accordingly, it is preferred that the inhibitors of the present invention reduce the kinase activity of PTK2 about 5%, 10%, 20%, 30%, 40%, 50%, 60%, 70%, 80%, 90% or even 100%, for example under conditions which are similar or identical to the test system disclosed herein (for example the PTK2 enzyme test).

PTK2 Enzyme Test

This test uses active PTK2 enzyme (Invitrogen Code PV3832) and poly-Glu-Tyr (4:1, Sigma P-0275) as the kinase substrate. The kinase activity is detected by means of the phosphorylation of the substrate in a DELFIA™ assay. The phosphorylated substrate is detected with the europium-labelled phosphotyrosine antibody PT66 (Perkin Elmer, No.: AD0040). In order to determine concentration-activity curves with PTK2 inhibitors the compounds are serially diluted in 10% DMSO/$H_2O$ and 10 µL of each dilution are dispensed per well in a 96-well microtitre plate (clear U-shaped base plate, Greiner No. 650101) (the inhibitors are tested in duplicates) and mixed with 10 µL/well of PTK2 kinase (0.01 µg/well). PTK2 kinase is diluted accordingly beforehand with kinase dilution buffer (20 mM TRIS/HCl pH 7.5, 0.1 mM EDTA, 0.1 mM EGTA, 0.286 mM sodium orthovanadate, 10% glycerol with the addition of freshly prepared BSA (fraction V 1 mg/mL) and DTT (1 mM)). The test compound and the PTK2 kinase are pre-incubated for 1 h at RT and shaken at 500 rpm. Then 20 µL ATP Mix (30 mM TRIS/HCl pH 7.5, 0.02% Brij, 0.2 mM sodium orthovanadate, 10 mM magnesium acetate, 0.1 mM EGTA, 1× Phosphatase Inhibitor Cocktail 1 (Sigma, No.: P2850), 50 µM ATP (Sigma, No.: A3377; 15 mM stock solution)) are added. The reaction is started by the addition of 10 µL/well of poly (Glu, Tyr) substrate (25 µg/well poly (Glu, Tyr), 0.05 µg/well biotinylated poly (Glu, Tyr) dissolved in 250 mM TRIS/HCl pH 7.5, 9 mM DTT)—the final concentration of DMSO is 2%. After 1 h kinase reaction (the plates are shaken at 500 rpm), the reaction is stopped by the addition of 12 µL/well of 100 mM EDTA, pH 8. And shaken for a further 5 min at RT (500 U/min).

55 µL of the reaction mixture are transferred into a streptavidin plate (Strepta Well High Bind (transparent, 96-well) made by Roche, No.: 11989685001) and incubated for 1 h at RT (shaking at 500 rpm). Then the microtitre plate is washed three times with 200 µL/well D-PBS (Invitrogen, No.: 14190). 100 µL of 1:2000 diluted DELFIA Eu-NI Anti-Phosphotyrosine PT66 antibody (Perkin Elmer, No.: AD0040, 1:2000 diluted in DELFIA test buffer (Perkin Elmer, No.: 1244-111)) is then added and it is incubated for 1 h at RT (shaking at 500 rpm). Then the plate is washed three times with 200 µL/well DELFIA washing buffer (Perkin Elmer, No.: 1244-114), 200 µL/well strengthening solution (Perkin Elmer, No.: 1244-105) is added and the whole is incubated for 10 min at RT (shaking at 300 rpm).

The time-delayed europium fluorescence is then measured in a microtitre plate reader (Victor, Perkin Elmer). The positive control consists of wells that contain solvent (2% DMSO in test buffer) and display uninhibited kinase activity. Wells that contain test buffer instead of enzyme act as a control for the background kinase activity. The $IC_{50}$ values are determined from concentration-activity analyses by iterative calculation using a sigmoidal curve analysis algorithm (FIFTY, based on GraphPAD Prism Version 3.03) with a variable Hill coefficient.

Further assays which might be used to identify PTK2 inhibitors are well-known to the skilled person and include inter alia a PTK2 soft agar assay or a Phospho-PTK2 (pY397) Assay. Both assays are explained in detail herein below.

PTK2 Soft-Agar Assay

This cellular test is used to determine the influence of PTK2 inhibitors on the growth of PC-3 prostate carcinoma cells in soft agar ('anchorage-independent growth'). After an incubation time of two weeks the cell vitality is demonstrated by Alamar Blue (resazurin) staining. PC-3 cells (ATCC CRL-1435) are grown in cell culture flasks (175 cm$^2$) with F12 Kaighn's Medium (Gibco, No.: 21127) which has been supplemented with 10% foetal calf serum (Invitrogen, No.: 16000-044). The cultures are incubated in the incubator at 37° C. and 5% $CO_2$ and are run twice a week. The test is carried out in microtitre plates (Greiner, No.: 655 185) and consists of a lower layer made up of 90 µL of medium with 1.2% agarose (Invitrogen, 4% agarose gel 1× liquid 40 mL, No.: 18300-012), followed by a cell layer in 60 µL medium and 0.3% agarose and finally a top layer comprising 30 µL medium which contains the test compounds (without the addition of agarose). To prepare the lower layer, 4% agarose are decocted with 10×D-PBS (Gibco, No.: 14200) and $H_2O$ and thus prediluted on 3% agarose in 1×D-PBS. The latter is adjusted with culture medium (F12 Kaighn's/10% FCS) and FCS to a final dilution of 1.2% agarose in F12 Kaighn's Medium with 10% FCS. Each well of a microtitre plate is supplied with 90 µL of the suspension for the lower layer and cooled to RT for 1 h. For the cell layer, PC-3 cells are detached using trypsin (Gibco, 0.05%; No.: 25300), counted and seeded in 60 µL F12 Kaighn's (10% FCS) with the addition of 0.3% agarose (37° C.). After cooling to RT for 1 h the test compounds (30 µL from serial dilutions) are added for quadruple measurements. The concentration of the test compounds usually covers a test range of between 10 µM and 0.3 nM. The compounds (stock solution: 10 mM in 100% DMSO) are prediluted in F12 Kaighn's Medium+6% DMSO, to obtain a final concentration of 1% DMSO. The cells are incubated at 37° C. and 5% $CO_2$ in a steam-saturated atmosphere for 14 days. The metabolic activity of living cells is then demonstrated with the dye Alamar Blue (AbD Serotec, No.: BUFO 12B). To do this, 18 µL/well of an Alamar Blue suspension are added and the whole is incubated for approx. 8 h in the incubator at 37° C. The positive control consists of empty wells that are filled with a mixture of 18 µL of Alamar Blue reduced by autoclaving and 180 µL of F12 Kaighn's Medium (10% FCS). The fluorescence intensity is determined by means of a fluorescence spectrometer (SpectraMAX GeminiXS, Molecular Devices). The excitation wavelength is 530 nm, the emission wavelength is 590 nm.

The $EC_{50}$ values are determined from concentration-activity analyses by iterative calculation using a sigmoidal curve analysis algorithm (FIFTY, based on GraphPAD Prism Version 3.03) with a variable Hill coefficient.

Phospho-PTK2 (pY397) Assay

This cellular test is used to determine the influence of PTK2 inhibitors on the state of the PTK2 phosphorylation at tyrosine 397 (pY397).

PC-3 cells (prostate carcinoma, ATCC CRL-1435) are grown in cell culture flasks (175 cm$^2$) with F 12 Kaighn's Medium (Gibco, No.: 21127) with the addition of 10% foetal calf serum (Invitrogen, No.: 16000-044). The cultures are incubated in the incubator at 37° C. and 5% $CO_2$ and run twice a week.

For the test, 2×104 cells pro well/90 µL medium are plated out in 96-well microtitre plates (Costar, No.: 3598) and incubated overnight in the incubator at 37° C. and 5% $CO_2$. The test compounds (10 µL from serial dilution) are added the next day. The concentration of the test compounds usually covers a range of 50 µM and 0.8 nM. The test compounds (stock solution: 10 mM in 100% DMSO) are diluted in medium/medium 10% DMSO such that the final concentration is 1% DMSO. The cells are then incubated in the incubator at 37° C. and 5% $CO_2$ for 2 h. Then the culture supernatant is removed and the cells are fixed with 150 µL 4% formaldehyde in D-PBS for 20 min at RT. The cell lawn is washed five times with 200 µL 0.1% Triton X-100 in D-PBS for 5 min in each case and then incubated for 90 min with blocking buffer (5% skimmed milk powder (Maresi Fixmilch) in TBST (25 mM Tris/HCl, pH 8.0, 150 mM NaCl, 0.05% Tween 20). The blocking buffer is replaced by 50 µL of the first antibody anti-phospho PTK2 [pY397] rabbit monoclonal (Invitrogen/Biosource, No.: 44-625G), which is diluted 1:200 in blocking buffer. For control purposes, alternatively a PTK2 [total] antibody (clone 4.47 mouse monoclonal, Upstate, No.: 05-537), diluted 1:400 in blocking buffer is used. This incubation is carried out at 4° C. overnight. Then the cell lawn is washed five times with 100 µL of 0.1% Tween in D-PBS for 5 min in each case and 50 µL/well of second antibody are added. In order to detect bound phospho-PTK2 [pY397] antibody a goat-anti-rabbit antibody is used which is coupled with horseradish peroxidase (Dako, No.: P0448; 1:500 dilution in blocking buffer). In order to detect bound PTK2 [total]-antibodies a rabbit-anti-mouse antibody is used, which is also coupled with horseradish peroxidase (Dako, No.: P0161; 1:1000 dilution in blocking buffer). This incubation is carried out for 1 h at RT with gentle shaking. The cell lawn is then again washed five times with 100 µL of 0.1% Tween in D-PBS for 5 min in each case. Peroxidase staining is carried out by adding 100 µL staining solution (1:1 mixture of TMB peroxidase substrate (KPL, No.: 50-76-02) and peroxidase solution B ($H_2O_2$) (KPL, No.: 50-65-02). The development of the stain takes place for 10-30 min in the dark. The reaction is stopped by the addition of 100 µL/well of a 1 M phosphoric acid solution. The absorption is determined photometrically at 450 nm with an absorption measuring device (VICTOR PerkinElmer). The inhibition of the anti-phospho PTK2 [pY397] immune staining is used to determine EC50 values. The staining with anti-PTK2 [total]-antibodies is for control purposes and should remain constant under the influence of inhibitor. The EC50 values are determined from concentration-activity analyses by iterative calculation with the aid of a sigmoidal curve analysis algorithm (FIFTY, based on GraphPAD Prism Version 3.03) with a variable Hill coefficient.

Compounds which effect a reduction of the amount of active PTK2 in cells, in tissues comprising said cells or subjects comprising said tissues or cells are likewise envisaged as PTK2 inhibitors and comprise, for example, aptamers, antibodies or functional fragments thereof which are able to bind to and thereby to inhibit PTK2; antisense oligonucleotides, iRNA, miRNA or siRNA which specifically bind to the nucleotides sequences encoding PTK2 and thereby reduce the amount of active PTK2 in a cell or a tissue. Such antibodies and interfering nucleic acid sequences are well-known to the skilled person; plenty of them are even commercially available.

Examples of PTK2 inhibitors which are envisaged in the context of the present invention are the compounds which are exemplified in WO 2010/106097, WO 2010/136559, WO 2011/039344, WO 2007/063384, WO 2010/058032, WO 2010/058030, WO 2010/055117, WO 2009/07153, WO 2005/1110245, WO 2008/129380, WO 2007/072158, WO 2005/111022, WO 2005/111023, WO 2005/111016, WO 2004/056807, WO 2009/071535, WO 2004/056786, WO 2010/062578, EP 2047849, WO 2008/115369, WO 2009/024332, WO 2008/129380, WO 2007/072158, WO 2004/056807, WO 2006/021457, WO 2010/062578, WO 2009/105498, WO 2004/030620, US 2008/167368, and/or WO 2009/153589 although the invention is in no way limited thereto. The aforementioned documents are included herein in their entirety by way of reference thereto.

In the context of the present invention, the term "PTK2 inhibitor" is interchangeable with the term "PTK2 antagonist" or the like.

PTK2 inhibitors show efficacy in a variety of experimental models of cancer, in particular in human cancer xenograft models in immunodeficient mice. However, their efficacy varies widely among different cancer models: whereas cancer regression or complete inhibition of growth can be achieved in some models, treatment of other cancer types results in partial inhibition of growth and some cancers are not affected at all. The present invention is based in essence on the surprising finding that the level of expression of E-cadherin protein in cancer cells from epithelial cancers can be used to predict the sensitivity of the respective cancers to PTK2 inhibitors when scored by way of the scoring system as established by the present invention. In view of that, it is envisaged to detect the expression of E-cadherin protein in a cancer sample from a patient, wherein an E-cadherin protein immunoreactivity score (IRS) of 0-2, preferably of 0-1, more preferably an IRS score of 1 and even more preferably of 0, indicates that the cancer/cancer patient is susceptible to treatment with a PTK2 inhibitor.

Said IRS score is preferably evaluated (detected) by way of an IHC method, although other immunological methods are not excluded.

An "IHC method" means the detection of targets (e.g. antigens) in tissue sections by the use of binding domains as specific reagents through target-binding domain interactions that are visualized by a label. It is envisaged that said tissue sections (which are for example about 2-5 µm in thickness) are taken from a tissue sample that has been preferably embedded, for example in paraffin. IHC protocols describing details of the methods of detection and the sources of the E-cadherin antibodies are described below. The IHC method used in the examples was the indirect avidin-biotin complex (ABC) immunoperoxidase method with DAB as a substrate for the reaction. Further IHC methods are explained in more detail herein below.

The term "binding domain" characterizes in connection with the present invention a domain of a polypeptide which specifically recognizes E-cadherin. The term "specifically recognizing E-cadherin" or "specific for E-cadherin", means in accordance with the present invention that the binding domain, e.g. an antibody, is capable of specifically interacting with and/or binding to E-cadherin. As used herein, the term "binds" in connection with the interaction between E-cadherin and a binding domain indicates that the binding domain associates with (e.g., interacts with or complexes with) E-cadherin to a statistically significant degree as compared to association with proteins generally (i.e., non-specific binding). Thus, the term "binding domain" is also understood to refer to a domain that has a statistically significant association or binding with E-cadherin.

A preferred example of a binding domain in line with the present invention is or comprises an epitope binding domain, preferably an antibody, more preferably a monoclonal antibody or an antigen binding fragment thereof.

The term "antibody" refers to a monoclonal or a polyclonal antibody (see Harlow and Lane, "Antibodies, A Laboratory Manual", CSH Press, Cold Spring Harbor, USA, 1988) which binds to a target, or a derivative of said antibody which retains or essentially retains its binding specificity. Preferred derivatives of such antibodies are chimeric antibodies comprising, for example, a mouse or rat variable region and a human constant region. The term "antibody" also comprises bifunctional (bispecific) antibodies and antibody constructs, like single-chain Fvs (scFv) or antibody-fusion proteins. The term "scFv fragment" (single-chain Fv fragment) is well understood in the art and preferred due to its small size and the possibility to produce such fragments recombinantly. Said antibody or antibody binding portion is for example a rat, mouse, camel, goat, sheep, chicken, horse, or human antibody or a humanized antibody. The term "humanized antibody" means, in accordance with the present invention, an antibody of non-human origin, where at least one complementarity determining region (CDR) in the variable regions such as the CDR3 and preferably all 6 CDRs have been replaced by CDRs of an antibody of human origin having a desired specificity. Optionally, the non-human constant region(s) of the antibody has/have been replaced by (a) constant region(s) of a human antibody. Methods for the production of humanized antibodies are described in, e.g., EP-A1 0 239 400 and WO90/07861. The term antibody or functional fragment thereof also includes heavy chain antibodies and the variable domains thereof, which are mentioned in WO 94/04678, WO 96/34103 and WO 97/49805, WO 04/062551, WO 04/041863, WO 04/041865, WO 04/041862 and WO 04/041867; as well as domain antibodies or "dAb's", which are based on or derived from the heavy chain variable domain (VH) or the light chain variable domain (VL) of traditional 4 chain antibody molecules (see, e.g., Ward et al. 1989 Nature 341, 544-546).

The term "antigen binding fragment" as used herein refers to fragments of the antibodies as specified herein which retain or essentially retain the binding specificity of the antibodies like, separated light and heavy chains, Fab, Fab/c, Fv, Fab', F(ab')2. An antigen-binding fragment may comprise a light chain variable region (VL) and a heavy chain variable region (VR) of an antibody; however, it does not have to comprise both. Fd fragments, for example, have two VH regions and often retain antigen-binding function of the intact antigen-binding fragment.

The following exemplary antibodies can be employed in the embodiments of the present invention. The invention is however not limited to these specific antibodies:

Mouse monoclonal antibody [HECD-1] to extracellular domain of E-cadherin (Abcam Ab1416).

Mouse monoclonal antibody to E-cadherin (Dako M3612) recognizes the 120 kD mature form and 82 kD fragment of E-cadherin Mouse Anti-E-cadherin monoclonal antibody (Invitrogen 18-0223); reacts with the cytoplasmic domain of human E-cadherin.

Mouse monoclonal antibody to E-cadherin (Sigma-Aldrich WH0000999M1)

Rabbit polyclonal antibody to E-cadherin (Cell Signalling 4065)

The term "epitope binding domain" includes, besides antibodies or antigen binding fragments thereof (sometimes also denoted as "functional fragments"), other binding entities which bind to (specifically bind to) a proteinaceous target such as E-cadherin. The term "epitope binding domain" includes, for example, a domain antibody (dAb), for example a human, camelid or shark immunoglobulin single variable domain or it may be a domain which is a derivative of a scaffold selected from the group consisting of CTLA-4 (Evibody); lipocalin; Protein A derived molecules such as Z-domain of Protein A (Affibody, SpA), A-domain (Avimer/Maxibody); Heat shock proteins such as GroEI and GroES; transferrin (trans-body); ankyrin repeat protein (DARPin); peptide aptamer; C-type lectin domain (Tetranectin); human γ-crystallin and human ubiquitin (affilins); PDZ domains; scorpion toxin kunitz type domains of human protease inhibitors; and fibronectin (adnectin); which has been subjected to protein engineering in order to obtain binding to a ligand other than the natural ligand. CTLA-4 (Cytotoxic T Lymphocyte-associated Antigen 4) is a CD28 family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies. For further details see Journal of Immunological Methods 248 (1-2), 31-45 (2001).

The binding domain of the present invention is either labeled or unlabeled.

A label refers in the context of the invention to a compound or composition detectable by spectroscopic, photochemical, biochemical, immunochemical, or chemical means.

The label may be directly or indirectly detectable.

"Directly" means that the label as such generates the signal such as a radioactive, chromogenic, or fluorescent signal. Direct labels include radiolabels, fluorescent label, electron-dense reagents; etc. The direct label has or generates a measurable signal that can be used to quantify and/or detect (qualitatively) the bound binding domain.

"Indirectly" means that the label is for example bound by another entity which as such is then detectable (detection entity). Indirect detection or indirect label involves the binding of a second directly or indirectly detectable binding domain to the indirect label. For example, the indirect label of the binding domain of the invention can be the ligand of a binding partner, such as biotin, which is a binding partner for streptavidin, or a nucleotide sequence, which is the binding partner for a complementary sequence, to which it can specifically hybridize etc. "Indirect labelling" is therefore characterized in that the primary binding domain is manipulated such that it can be detected by a second binding domain (sometimes also denoted detection entity) which is specific for that manipulation (e.g. a biotin label).

In a preferred embodiment said binding domain is an antibody (primary antibody) and said detection entity is a secondary antibody which specifically reacts with the primary antibody as such or the label of the primary antibody.

It is also envisaged that indirect and direct labelling is mixed. For example, already the direct label is able to generate a signal (e.g. a fluorescent label like FITC) but the secondary binding domain, which is also labelled, e.g. with a direct label binds specifically to that label (anti FITC antibody) binds to the label of the primary signal and, thereby, may increase the detectable signal. Such means and methods are well-known to the skilled person, in particular to practitioners in the field of immunochemistry.

In another embodiment, the primary binding domain (e.g. an antibody) is not labeled as such but is detected/detectable by way of a secondary binding domain (detection entity) which binds to the primary binding domain (for example a primary non-labeled antibody raised in mouse is detected by a second, labeled antibody, which was raised in another species and specifically binds to mouse antibodies (e.g. goat anti-mouse)). The secondary binding domain is then directly or indirectly labeled. Such antibody detection sandwiches are well-established and the skilled person will have no problem to generate/establish or create such systems.

The "detection" (sometimes also denoted as "determination" and grammatical variants thereof) which takes place ex vivo is carried out by standard detection techniques which are well-known to the skilled person and include, but are not limited to, any kind of suitable IHC detection techniques, such as light and fluorescence-based microscopy including near infrared based microscopy, and confocal microscopy.

The term "ex vivo", which is interchangeable with "in vitro" refers to activities conducted in cells in a controlled environment. The methods of the present invention are conducted ex vivo.

As mentioned hereinbefore, immunohistochemistry (IHC) is the detection of targets (in the context of the present invention e.g. E-cadherin) and/or subsets of cells presenting said target in tissue sections by the use of binding domains which are either directly labeled (direct IHC) or indirectly labeled (indirect IHC), which binding domains react with their target through specific target-binding domain interactions. In the context of the present invention, said target is E-cadherin.

These interactions are then visualized by the mentioned label. There are mainly two strategies used for the immunohistochemical (IHC) detection of antigens in tissue, the direct method and the indirect method. The direct method of IHC uses one directly labelled binding domain, which binds directly to the target being stained for. The direct method is thus a one-step staining method, and involves e.g. a labelled antibody (e.g. FITC conjugated antiserum) reacting directly with the antigen in tissue sections. This technique utilizes only one antibody and the procedure is therefore simple and rapid. The indirect method of IHC uses one binding domain against E-cadherin, and a second, labelled, binding domain against the first binding domain. A second binding domain is for example an antibody raised against the IgG of the animal species in which the primary antibody has been raised.

It is envisaged that in some embodiments of the methods of the present invention, said IHC method is characterized by the following steps:
(a) optionally providing a cancer sample (or, alternatively, optionally providing a container comprising a cancer sample);
(b) fixation of said cancer sample;
(c) optionally embedding the cancer sample in paraffin;
(c) incubation of the fixed cancer sample with an E-cadherin specific binding domain;
(d) directly or indirectly detecting the binding domain and thereby the E-cadherin expression on the cancer cells.

"Fixing" or "fixation" means a fixation procedure which is suitable to prepare the cancer sample for a subsequent IHC detection procedure. A "fixation" is particularly carried out in order to ensure the preservation of tissue architecture and cell morphology. Suitable fixation conditions are well-known and also disclosed herein. Alternatively, it is also envisaged that the tissue/subset is preserved by way of deep-freezing (e.g. in liquid nitrogen).

All the above pre-treatment steps/measures are within the scope of the term "fixation", i.e. fixation specifically includes fixation with fixing agents like formaldehyde, paraformaldehyde; and/or deep-freezing of the tissue sample/subset of cells, and/or optionally also the embedding of the tissue/subset of cells in paraffin or similar agents.

Means and methods to put the different IHC protocols into practice are well-known to the skilled person. See for example the respective protocols in the literature or in the internet (for example www.ihcworld.com).

The most common fixative used for immunohistochemistry is paraformaldehyde, which is frequently used in diverse buffers containing about 1 to 5% paraformaldehyde. Specific buffers which are based on paraformaldehyde are exemplified in the following:
a) 4% paraformaldehyde in 0.1 M phosphate buffer
b) 2% paraformaldehyde with 0.2% picric acid in 0.1 M phosphate buffer
c) PLP (paraformaldehyde, lysine, paraformaldehyde) fixative: e.g. 4% paraformaldehyde, 0.2% periodate and 1.2% lysine in 0.1 M phosphate buffer
d) 4% paraformaldehyde with 0.05% glutaraldehyde.

These buffers are not intended to limit the invention but simply illustrate specific conditions which are normally applied to achieve a sufficient fixation of tissue. The standard fixation time is about 5, 10, 15, 20, 30 min to overnight. The so-treated tissue is frequently subject to a subsequent paraffin embedding protocol, followed by the incubation in organic solvents like for example xylene and ethanol treatment. The sample is then normally hydrated by placing it in 95%, 70%, 50%, 30% alcohol (e.g. ethanol) for several minutes each. There is, however, no standard protocol for IHC, i.e. the protocol will vary depending on the tissue, the binding domains used etc. All this is known to the skilled person and routinely handled without further ado. Specific protocols are disclosed for example in the internet (searchable with the string "IHC protocols" in a search machine like Google etc.). Some antigens will not even survive moderate amounts of aldehyde fixation. Under this condition, tissues are often fresh frozen in liquid nitrogen and cut with a cryostat. The sections are kept frozen at −20° C. or lower until fixation with cold acetone or alcohol.

Once a "signal" is obtained, proving that signal truly reflects the distribution of the target is still a matter of some difficulty. The simplest negative control is the absence of expression in tissues in which the RNA for E-cadherin is known not to be expressed. An alternative negative control is the elimination of the signal by pre-incubating the binding domain with an excess of the peptide or protein with which it was raised.

It is also envisaged that the IHC methods of the present invention are combined with other techniques which are applicable on tissue sections, such as in situ hybridization techniques (e.g. fluorescent in situ hybridization), in order to verify or detect further cancer associated signals and or other intracellular signals of cancer cells.

Methods, for example IHC methods, which can be employed in the context of the present invention are disclosed herein and exemplified in the appended examples.

The gist of the present invention is in essence the surprising finding that the level of expression of E-cadherin protein in cancer cells can be used to predict the sensitivity of the respective cancers to PTK2 inhibitors. In view of that, it is envisaged to detect the expression of E-cadherin protein in a cancer/in a cancer sample from a patient, wherein an E-cadherin protein immunoreactivity score (IRS) of 0-2, preferably an IRS score of 0-1, more preferably an IRS score of 1 and even more preferably an IRS score of 0 indicates that the cancer/cancer patient is susceptible to treatment with a PTK2 inhibitor.

The IRS score of the present invention was established as follows. We have assessed the number of membrane-bound E-cadherin positive cancer cells using paraform-aldehyde-fixed and paraffin-embedded tissue samples. The cancers used were derived from xenograft models of human cancer cell lines grown in nude mice (BomTac:NMRI-Foxn1nu), including pancreatic cancer cell lines MiaPaCa-2 and BxPC-3; prostate cancer cells PC-3 and ovarian cancer cells TOV-21G.

The entire section from each sample was analyzed and an average of the percentage of E-cadherin positive cancer cells determined as the number of E-cadherin positive cells over the total number of cancer cells in all the histologic fields examined. Only membrane E-cadherin immunoreactivity in cancer cells was considered positive for scoring purposes. The person skilled in the art of pathology understands which cells are relevant under the conditions present when performing the method and may determine the fraction of positive cells based on his/her general knowledge and the teachings of the present disclosure.

The scoring as proposed here is semi-quantitative; the protein expression levels are recorded as 0, 1, 2, 3 or 4 with 0 being substantially no detectable protein expression (less than 1%) and 4 being the highest detected protein expression (>60%).

As positive control, tissue sections from normal colonic mucosa and/or colorectal cancer samples known to express E-cadherin could be included. The connective tissue present in any given tissue (normal and tumor) could serve as a negative control in these assays.

The mentioned "control", "positive control" or "control sample" is preferably a sample (cell or tissue) which allows a comparison with the test sample, for example because both samples are mainly composed of the same cell type (e.g. both consist of epithelial cells) or both samples are derived from the same tissue yet from a different source. "A different source" includes e.g. a cell/tissue sample obtained from a healthy subject, preferably from a subject who does not suffer from a cancer or a cell/tissue sample obtained from a distinct part of the same subject wherein said distinct part appears to be free from associated symptoms of a cancer.

The number of E-cadherin positive cancer cells was scored as follows:
0 (less than 1%), 1 (about 1-10%), 2 (about 11-30%), 3 (about 31-60%), 4 (>60%).

"Positive cells" thereby means cancer cells showing E-cadherin expression as explained herein above. The scoring mentioned herein applies to all embodiments of the present invention. Preferably, an E-cadherin protein immunoreactivity score (IRS) of IRS-0 is characterized by an average of less than 1% membrane E-cadherin positive cancer cells over the total number of cancer cells in one or more histologic field(s) examined; IRS-1 is characterized by an average of about 1-10% membrane E-cadherin positive cancer cells over the total number of cancer cells in one or more histologic field(s) examined; IRS-2 is characterized by an average of about 11-30% membrane E-cadherin positive cancer cells over the total number of cancer cells in one or more histologic field(s) examined; IRS-3 is characterized by an average of about 31-60% membrane E-cadherin positive cancer cells over the total number of cancer cells in one or more histologic field(s)

examined; and IRS-4 is characterized by an average of more than 60% membrane E-cadherin positive cancer cells over the total number of cancer cells in one or more histologic field(s) examined. The mentioned scoring is, in a preferred embodiment, conducted via IHC using paraformaldehyde-fixed and paraffin-embedded tissue samples.

"One or more" includes in this regard 1, 2, 3, 4, 5, 6, 7, 8, 9 or even more histological fields which are analysed (preferably per sample), depending on the circumstances. At least "3" histological fields are preferred.

When testing the above mentioned xenograft models of human cancer cell lines grown in nude mice, we could demonstrate that PTK2 inhibitors where highly efficacious in certain models whereas the response in others was rather low. The xenograft models were established as follows: Athymic female BomTac:NMRI-Foxn1nu mice about six weeks of age were allowed to adjust to the new environment for at least 3 days before they were used for experiments. The animals were housed under standardized conditions in groups of 5 in Macrolon® type II cages. Standardized diet (PROVIMI KLIBA) and autoclaved tap water were provided ad libitum. To establish subcutaneous tumors, cells were harvested by trypsinization, centrifuged, washed and resuspended in ice-cold PBS+5% FCS. 100 µL cell suspension containing 5,000,000 cells was then injected subcutaneously into the right flank of the nude mice (1 site per mouse). Mice were randomly distributed between the treatment and the vehicle control group (10-14 days after cell injection) when tumors were well established and had reached diameters of 6-9 mm. The tumor diameter was measured three times a week (Monday, Wednesday and Friday) with a caliper. The volume of each tumor [in mm$^3$] was calculated according to the formula "tumor volume=length*diameter2*π/6". To monitor side effects of treatment, mice were inspected daily for abnormalities and body weight was determined three times a week (Monday, Wednesday and Friday). Animals were sacrificed at the end of the study about three weeks after start of treatment. Animals with necrotic tumors or tumor sizes exceeding 2000 mm$^3$ were sacrificed early during the studies for ethical reasons.

When testing the above mentioned xenograft models of human cancer cell lines grown in nude mice, we could demonstrate that PTK2 inhibitors where highly efficacious in certain models whereas the response in others was rather low. For example the human pancreatic adenocarcinoma model derived from the cell line MiaPaCa-2 was highly responsive to treatment with PTK2 inhibitors resulting in strong inhibition of cancer growth (i.e. "tumor growth inhibition" or TGI), indicated by a TGI of 114% and the occurrence of cancer regressions. Tissue sections were prepared from this cancer and stained by immunohistochemistry with an antibody against E-cadherin. Protein expression of E-cadherin was completely absent in these cancer sections corresponding to an IRS of "0" (<1% E-cadherin positive cells). TGI is defined herein below. In contrast, two further pancreatic adenocarcinoma models derived from the cell lines BxPC-3 or AsPC-1 showed only weak or no sensitivity following the treatment with PTK2 inhibitors with TGIs of 49% (BxPC-3) and 13% (AsPC-1) and the complete absence of cancer regressions. Immunohistochemistry of tissue sections from these cancer models with antibodies against E-cadherin demonstrated a strong expression of E-cadherin in these cancers corresponding to the IRS of "4" (>60% positive cells) for BxPC-3 and "3" (31-60% positive cells) for AsPC-1 (see FIG. 2 for further illustration). It is therefore envisaged that these adenocarcinoma models could serve as a reference/reference sample for the evaluation and/or adjustment of the IRS score of the present invention. A BxPC-3 xenograft could be seen as a reference for an IRS score of "4" while an AsPC-1 xenograft may serve as a reference for IRS score "3". Likewise "MiaPaCa-2", could serve as a reference for an E-cadherin IRS of "0". The generation of such xenografts is described herein.

The above data show that a minor or absent expression of E-cadherin corresponds with the sensitivity of preclinical cancer models to PTK2 inhibitors whereas cancers with an intermediate to high percentage of E-cadherin expressing cancer cells seem to be less sensitive or insensitive. In view of that, it could be established that an E-cadherin protein immunoreactivity score 0-2, preferably an IRS score of 0-1, and even more preferably an IRS score of 0 indicates that the cancer/cancer patient is susceptible to treatment with a PTK2 inhibitor.

The "tumor growth inhibition" or "TGI" is defined as follows:

$$TGI = 100 * \frac{(C_d - C_1) - (T_d - T_1)}{(C_d - C_1)},$$

wherein "$C_1$" and "$T_1$" means median tumor volumes in control and treatment group at start of the experiment at day 1, and "$C_d$" and "$T_d$" means median tumor volumes in control and treatment group at end of the experiment at day d.

In a further embodiment, the present invention relates to a method of treating a patient with a cancer having an E-cadherin protein immunoreactivity score 0-2, preferably an IRS score of 0-1, more preferably an IRS score of 1 and even more preferably an IRS score of 0, comprising administering to the patient a therapeutically effective amount of a PTK2 inhibitor.

It will be understood that within the context of the embodiments of the present invention, the E-cadherin protein immunoreactivity score is preferably evaluated by way of an IHC method as indicated above and exemplified herein. Suitable IHC methods are described herein although the present invention is not limited to these specific protocols.

By "therapeutically effective amount" or "therapeutically active" is meant a dose of a PTK2 inhibitor that produces the therapeutic effects for which it is administered. The therapeutically effective amount of the drug may reduce the number of cancer cells, reduce the cancer size, inhibit (i.e., slow to some extent and preferably stop) cancer cell infiltration into peripheral organs, inhibit (i.e., slow to some extent and preferably stop) cancer metastasis, inhibit, at least to some extent, cancer growth, and/or relieve to some extent one or more of the symptoms associated with the disorder. The exact dose will be ascertainable by one skilled in the art using known techniques. As is known in the art, adjustments for age, body weight, general health, sex, diet, drug interaction and the severity of the condition may be necessary, and will be ascertainable with routine experimentation by those skilled in the art.

It was shown for the first time by the present inventors that the E-cadherin protein immunoreactivity score of a cancer sample correlates well with the susceptibility of the respective cancer to PTK2 inhibitor treatment. Based on these findings, it is now possible to stratify cancer patients or cancers (or cancer cell lines) which are susceptible to a treatment with PTK2 inhibitors. Based on the findings of the present invention, it is now clear that patients whose cancers show an E-cadherin protein immunoreactivity score (IRS) of 0, 1 or 2 should preferentially be treated with PTK2 inhibitors, as the probability of achieving a therapeutic benefit will be higher for those patients than for patients with IRS 3 or 4. It is however envisaged that cancers having an E-cadherin protein immunoreactivity score of 3 or above 3 may also be treated with an PTK2 inhibitor, as the high IRS score (3-4) although clearly indicating a lower probability of achieving a therapeutic benefit for the patient with PTK2 inhibitors, does not necessarily exclude a residual therapeutic effect of these PTK2 inhibitors. Such patients could also be treated with alternative (alternative to PTK2 inhibitors) or additional anti-cancer therapies (i.e. therapies which are not based on PTK2 inhibitors). Additional or alternative anti-cancer therapies include, but are not limited to therapies which can be selected from antineoplastic agents, anti-angiogenic agents, chemotherapeutic agents and peptide cancer therapy agents. The antineoplastic agents can be selected from antibiotic-type agents, alkylating agents, antimetabolite agents, hormonal agents, immunological agents, interferon-type agents, kinase inhibitors, and combinations thereof. Such pharmaceutically active compound/agent is for example a traditional small organic chemical molecule or can be macromolecules such as a proteins, antibodies (including fragments thereof), peptibodies, DNA, RNA or fragments of such macromolecules.

The present invention further relates to a method for stratifying cancer patients that are susceptible to treatment with a PTK2 inhibitor, comprising determining the E-cadherin IRS score in a cancer sample of said patient, wherein an E-cadherin protein immunoreactivity score (IRS) of 0-2 (i.e. 2, 1, or 0) indicates that the cancer patient is susceptible to treatment with a PTK2 inhibitor. An E-cadherin protein immunoreactivity score (IRS) of 3-4 (i.e. 3, or 4) indicates that the patient is not susceptible to treatment with a PTK2 inhibitor or at least that the probability of achieving a therapeutic benefit for the patient with PTK2 inhibitors is rather low.

The term "stratify" or "stratifying" refers to sorting patients into those who are more (or less) likely to benefit from an anti-cancer therapy which is based on a PTK2 inhibitor than others. The methods of present invention may thus be employed for stratifying cancer patients with regard to their susceptibility to treatment with a PTK2 inhibitor. As mentioned, those patients whose cancers show an E-cadherin protein immunoreactivity scores IRS of 0-2, preferably an IRS score of 0-1, more preferably an IRS score of 1 and even more preferably an IRS score of 0 are more likely to benefit from said PTK2 inhibitor based therapy, while those whose E-cadherin protein immunoreactivity score (IRS) of the cancer is 3 or greater are less likely to benefit from such a therapy.

Specifically, a "patient who may benefit" from anti-cancer therapy with a PTK2 inhibitor is a patient in which a PTK2 inhibitor has a higher likelihood to have a therapeutic effect. The likelihood that (a) cancer and/or a cancer patient may or may not respond favorably is dependent on the E-cadherin protein immunoreactivity score on the cell membrane of the respective cancer cells of said patient, as described herein.

Correspondingly, a "patient who may not benefit" from anti-cancer therapy with a PTK2 inhibitor is a patient in which a PTK2 inhibitor does not have a higher likelihood to have a therapeutic effect.

The present invention further relates to the use of a PTK2 inhibitor as defined herein for the preparation of a pharmaceutical composition for the treatment of a cancer patient whose cancer is characterized by an E-cadherin protein immunoreactivity score of 0-2, preferably an IRS score of 0-1, and even more preferably an IRS score of 0.

Said pharmaceutical composition may further comprise pharmaceutically acceptable carriers and/or diluents. Examples of suitable pharmaceutically acceptable carriers and/or diluents are well known in the art and include phosphate buffered saline solutions, water, emulsions, such as oil/water emulsions, various types of wetting agents, sterile solutions etc. Compositions comprising such carriers can be formulated by well known conventional methods.

These pharmaceutical compositions of the present invention can be administered to a subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Furthermore, the pharmaceutical compositions of the invention may comprise further agents such as additional anti-cancer therapies/agents. Additional anti-cancer therapies include, but are not limited to therapies which can be selected from antineoplastic agents, anti-angiogenic agents, chemotherapeutic agents and peptide cancer therapy agents. The antineoplastic agents can be selected from antibiotic-type agents, alkylating agents, antimetabolite agents, hormonal agents, immunological agents, interferon-type agents, kinase inhibitors, and combinations thereof. Such pharmaceutically active compound/agent is for example a traditional small organic chemical molecule or can be macromolecules such as a proteins, antibodies (including fragments thereof), peptibodies, DNA, RNA or fragments of such macromolecules. Such therapies are well known to the skilled person.

The route of administration of the PTK2 inhibitors described herein or the pharmaceutical compositions of the present invention depends on the circumstances and includes (but is not limited to) oral administration, parenteral administration, e.g., intravenously, intramuscularly, intraperitonealy, etc., subcutan administration, transdermal administration, inhalative administration, by suppository etc.

In a further embodiment, the present invention relates to a PTK2 inhibitor as defined herein for use in the treatment of a cancer patient whose cancer is characterized by an E-cadherin protein immunoreactivity score of 0-2, preferably an IRS score of 0-1, more preferably an IRS score of 1, and even more preferably an IRS score of 0.

It is preferred that within the context of the present invention, the cancer patient is or has been identified (characterized or stratified) with a method as defined herein, preferably with the IHC method described herein. Said identification or stratification method may be carried out prior to and/or during said treatment with said PTK2 inhibitor.

The present inventors established that the E-cadherin protein immunoreactivity score of a cancer sample correlates very well with the susceptibility of the respective cancer to PTK2 inhibitor treatment. Based on this finding, it is now possible to select, based on the respective E-cadherin IRS, an appropriate anti-cancer therapy which is potentially therapeutically effective for a cancer patient suffering from cancer, and in particular for cancer patients suffering from a carcinoma.

Patients and/or cancers whose E-cadherin protein immunoreactivity score (IRS) is greater then 3 should, based on the findings of the present invention, be less susceptible to treatment with PTK2 inhibitors. These patients can additionally or alternatively be treated with alternative anti-cancer therapies, although it cannot be excluded that PTK2 inhibitors might still exert a beneficial effect in these patients. Thus, it is still possible to employ these compounds even in patients which are characterized by an E-cadherin IRS score of 3 or above, although it is expected that the respective PTK2 inhibitors will not be as effective in these patients as in patients which are characterized by an E-cadherin IRS of 2, preferably 1 and even more preferably 0. Accordingly, it is to be understood that by way of the present invention it is possible to select a more suitable therapy form depending on the respective E-cadherin IRS score.

The present invention therefore relates in a further embodiment to a method for selecting an anti cancer treatment for a cancer patient comprising the steps of:
  (a) determining the E-cadherin protein immunoreactivity score of a cancer sample of said patient; and
  (b) selecting preferably a PTK2 inhibitor as anti cancer treatment for said patient if the E-cadherin protein immunoreactivity score determined in (a) is 2, 1 or 0, (1 being preferred and 0 being more preferred), or
  (c) selecting preferably an alternative or an additional anti cancer treatment if the E-cadherin protein immunoreactivity score determined in (a) is 3 or 4.

"Selecting preferably a PTK2 inhibitor as anti cancer treatment" means that it is preferred to use a PTK2 inhibitor based therapy for cancers having an E-cadherin protein immunoreactivity score of 2, 1 or 0 (1 being preferred and 0 being more preferred). It is however envisaged that cancers having an E-cadherin protein immunoreactivity score of 3 or above 3 may also be treated with an PTK2 inhibitor, as the high IRS score (3-4) although clearly indicating a lower probability of achieving a therapeutic benefit for the patient with PTK2 inhibitors, does not necessarily exclude a residual therapeutic effect of these PTK2 inhibitor. In such cases (high IRS score of 3 or above), the PTK2 inhibitor is preferably not used alone.

Based on the novel findings of the present invention, namely that a cancer which is characterized by an E-cadherin protein immunoreactivity score of 2, 1 or 0 (1 being preferred and 0 being even more preferred) is susceptible to a PTK2 inhibitor, it is also envisaged to provide a screening method which employs cancer cells characterized by an E-cadherin protein immunoreactivity score of 2, 1 or 0 (1 being preferred and 0 being more preferred), to screen for PTK2 inhibitors, as these cancer cells are (more) susceptible to PTK2 inhibitors and thereby may enable the positive identification of novel PTK2 inhibitors which, otherwise (i.e. when employing cancer cells characterized by an E-cadherin protein immunoreactivity score of 3 or above 3), would have been sorted out.

Therefore, in a further embodiment, the present invention relates to a method of screening for a therapeutically effective PTK2 inhibitor comprising the following steps:
  (a) providing cancer cells or a cancer cell line which are characterized by an E-cadherin protein immunoreactivity score of 2, 1, or 0 (1 being preferred and 0 being even more preferred)
  (b) contacting the cancer cell or the cancer cell line of (a) with a PTK2 inhibitor; and
  (c) evaluating whether the PTK2 inhibitor negatively affects the cancer cell/cancer cell lines.

The above screening method is preferably a "phenotypical" screening method which employs phenotypically detectable changes of the cancer cells in response to the PTK2 inhibitor (these responses then indicate whether the PTK2 inhibitor is therapeutically effective or not). The term "phenotypically detectable changes" means changes which negatively affect the cancer cells. These negative effects includes cell death such as apoptosis or necrosis, reduced migration capabilities of the cancer cells/cancer cell lines and/or inhibition of proliferation of these cells, to name some. This list is however not exclusive, i.e. the skilled person is aware of further phenotypical changes of cancer cells which might indicate that a test compound actually negatively affects the respective cell. By way of the above screening method it is easier to identify therapeutically effective PTK2 inhibitors.

The present invention also relates to a pharmaceutical package comprising at least one PTK2 inhibitor, and:
  (a) instructions and/or an imprint indicating that said PTK2 inhibitor is preferably used for the treatment of patients which suffer from a cancer which is characterized by an E-cadherin protein immunoreactivity score of 2 or below 2; and/or
  (b) instructions and/or an imprint indicating that said patient is to be stratified by a method described herein; and/or
  (c) means to carry out a method as defined herein.

"Means to carry out a method as defined herein" includes inter alia E-cadherin specific antibodies, positive and/or negative controls as described herein elsewhere, buffers which may be used for IHC methods, and/or other means which can be used for the detection methods of the present invention, such as control antibodies, secondary antibodies, glass or plastic slides for IHC etc.

In a further embodiment, the present invention relates to a pharmaceutical kit or package comprising a PTK2 inhibitor and further comprising an E-cadherin antibody which is used for the prediction of the E-cadherin IRS.

In another embodiment, the present invention relates to a diagnostic kit or package comprising an E-cadherin antibody for the prediction of the E-cadherin IRS and a PTK2 inhibitor which is used for the treatment of patients which have been determined, characterized, identified or stratified in accordance with the methods of the present invention.

In a further aspect, the present invention relates to a kit, preferably a diagnostic kit or diagnostic package comprising means to detect E-cadherin protein expression in accordance with the means and methods of the present invention and:
  (a) package inserts and/or instructions as to carry out said E-cadherin detection (scoring); and/or
  (b) positive and/or negative controls which allow the verification of the score.

The term "package insert and/or instructions" is used to refer to instructions customarily included in commercial packages of diagnostic products that contain information about the methods, usage, storage, handling, and/or warnings concerning the use of such diagnostic products. "Positive controls" includes cancer cell or cancer samples expressing E-cadherin, or E-cadherin as such (protein control) which might be used in standard immunological methods as described herein. "Negative controls" includes reference cells or reference samples which do not express E-cadherin on the protein level. Both, the positive as well as the negative control could also be replaced by pictures indicating the respective score and thereby aiding the practitioner. "Means to detect E-cadherin protein expression" includes inter alia E-cadherin specific antibodies (i.e. antibodies binding to E-cadherin).

The present invention relates in a further embodiment to an E-cadherin antibody for use in the stratification of cancer patients with regard to their susceptibility to treatment with a PTK2 inhibitor. The stratification can be conducted in accordance with the methods of the present invention.

Likewise, the present invention relates to an E-cadherin antibody for use in a method for determining whether a cancer patient is susceptible to treatment with a protein tyrosine kinase 2 (PTK2) inhibitor. Said method comprises the detection of the expression of the E-cadherin protein in a cancer sample of said cancer patient, wherein an E-cadherin protein immunoreactivity score (IRS) of 0-2 indicates that the cancer patient is susceptible to treatment with a PTK2 inhibitor.

The present inventors established that the E-cadherin protein expression as evaluated for example by way of the protein immunoreactivity score as described herein, correlates very well with the susceptibility of the respective cancer to PTK2 inhibitor treatment. It is however assumed that the expression profile of the E-cadherin mRNA when evaluated in the respective cancer cells is likewise predictive for the susceptibility of the respective cancers/cancer patients to PTK2 inhibitor treatment. Thus, it has to be understood that gist of the present invention extends to the evaluation of the E-cadherin mRNA as well. Thus, all the embodiments of the present invention which are disclosed and described herein equally apply to the measurement of the expression level of E-cadherin mRNA in cancer cells. It is particularly assumed that a decreased expression of E-cadherin mRNA or no expression of E-cadherin mRNA indicates an increased susceptibility of the respective cancer/cancer patient to treatment with (a) PTK2 inhibitor(s). Methods which allow the skilled person to evaluate the expression profile of E-cadherin expressing cancer cells are well-known to the skilled person and include for example Northern blotting, mRNA profiling techniques including detection techniques based on nucleic acid arrays, polymerase chain reaction (PCR) techniques, such as real time quantitative PCR or "Q-PCR" etc. It will be understood that the present invention is not limited to these techniques which are merely exemplified to illustrate some of the techniques which are known to the skilled person. The term "quantitative PCR", or "Q-PCR", refers to a variety of methods used to quantify the results of the polymerase chain reaction for specific nucleic acid sequences. Such methods typically are categorized as kinetics-based systems, that generally determine or compare the amplification factor, such as determining the threshold cycle ($C_t$), or as co-amplification methods, that generally compare the amount of product generated from simultaneous amplification of target and standard templates. Many Q-PCR techniques comprise reporter probes, intercalating agents, or both. For example but not limited to TaqMan® probes (Applied Biosystems), i-probes, molecular beacons, Eclipse probes, scorpion primers, Lux™ primers, FRET primers, ethidium bromide, SYBR® Green I (Molecular Probes), and PicoGreen® (Molecular Probes). The skilled person is well aware how to measure the expression level of the respective E-cadherin mRNA.

This disclosure may best be understood in conjunction with the accompanying drawings, incorporated herein by references. Furthermore, a better understanding of the present invention and of its many advantages will be had from the following examples, given by way of illustration and are not intended as limiting.

Human tumor cells were seeded in chamber slides and stained with specific antibodies against human E-cadherin. Antibody binding was detected with a secondary antibody labeled with fluorescent dye (Alexa 488, green signal). Nuclear DNA was stained with propidium iodide (PI, red signal). E-cadherin was either absent or expressed in a small fraction of cells (see the MiaPaca2 and TOV-21G cell lines). In contrast, BxPC-3 cells displayed an epithelial phenotype with strong expression of E-cadherin.

Figure 2:
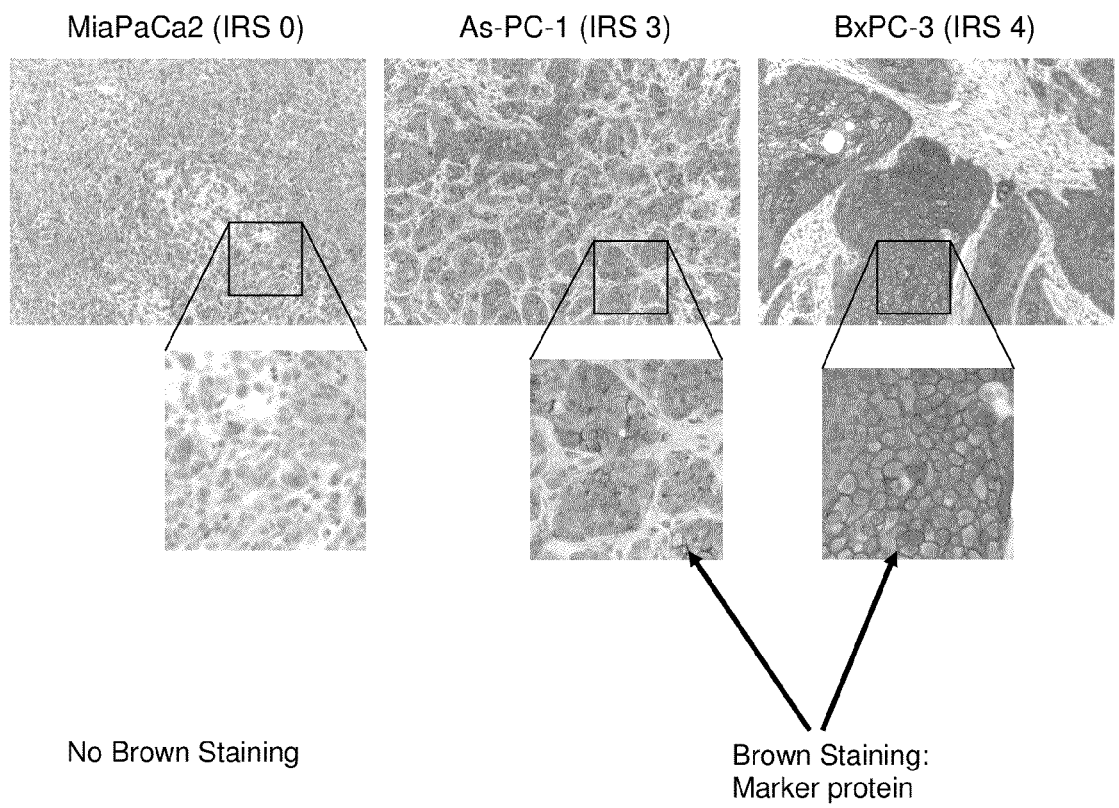

FIG. 2: E-Cadherin Expression in Xenograft Cancers

Five micrometer thick paraffin sections were obtained from xenograft cancers derived from MiaPaCa-2, As-PC-1 and BxPC3 cells and stained for E-cadherin using the ABC immunoperoxidase method followed by hematoxylin counterstaining. Brown staining in the membrane of tumor cells indicates the presence of the marker protein (no staining in MiaPaca2; brown staining in As-PC-1 (30%) and BxPC-3 (>60%)).

EXAMPLES

The following examples illustrate the invention. These examples should not be construed as to limit the scope of this invention. The examples are included for purposes of illustration and the present invention is limited only by the claims.

Example 1

Sensitivity of Human Tumor Xenografts to PTK2 Inhibitors

The xenograft models were established as follows: Athymic female BomTac:NMRI-Foxn1nu mice about six weeks of age were allowed to adjust to the new environment for at least three days before they were used for experiments. The animals were housed under standardized conditions in groups of 5 in Macrolon® type II cages. Standardized diet (PROVIMI KLIBA) and autoclaved tap water were provided ad libitum. To establish subcutaneous tumors, cells were harvested by trypsinization, centrifuged, washed and resuspended in ice-cold PBS+5% FCS. 100 µL cell suspension containing 5,000,000 cells was then injected subcutaneously into the right flank of the nude mice (1 site per mouse). Mice were randomly distributed between the treatment and the vehicle control group (10-14 days after cell injection) when tumors were well established and had reached diameters of 6-9 mm. The tumor diameter was measured three times a week (Monday, Wednesday and Friday) with a caliper. The volume of each tumor [in mm$^3$] was calculated according to the formula "tumor volume=length*diameter2*π/6". To monitor side effects of treatment, mice were inspected daily for abnormalities and body weight was determined three times a week (Monday, Wednesday and Friday). Animals were sacrificed at the end of the study about three weeks after start of treatment. Animals with necrotic tumors or tumor sizes exceeding 2000 mm$^3$ were sacrificed early during the studies for ethical reasons.

The sensitivity of human tumor xenografts growing in nude mice to treatment with PTK2 inhibitors was as follows:

| Cancer type | Model | TGI | Significant vs. controls | Regressions | Score |
|---|---|---|---|---|---|
| Pancreatic adenoca | MiaPaCa-2 | 114% | yes | yes | 0 |
| | AsPc-1 | 13% | no | no | 3 |
| Prostate ca | PC-3 | 102% | yes | yes | n.a. |
| Ovarian ca | TOV-21G | 100% | yes | yes | 0 |
| Pancreatic AC | BxPC-3 | 49% | yes | no | 4 |
| Colon ca | HCT-116 | 34% | no | no | 4 |
| | LoVo | 24% | no | no | 4 |
| | HT-29 | 7% | no | no | 4 |

Example 2

Immunohistochemistry Protocol (ABC Method) for Determining E-Cadherin Expression in Xenograft Models Deparaffinization:
   heat slides for 1 h at 65° C.;
   put slides in xylene for 3×5 min, then in 100% EtOH abs., 96% EtOH, 70% EtOH (3×20 sec each), then in dest. water;
Antigen Retrieval:
   put slides in citrate buffer for 20 min in an autoclave at 121° C./1 bar;
   allow slides to cool at RT for 30 min;
   wash with PBS;
Staining:
   incubate slides 5 min in 3% $H_2O_2$ in PBS;
   wash with PBS;
   add M.O.M. blocking reagent (2 drops=90 µL of stock in 2500 µL PBS) to the tissues, incubate 60 min at RT;
   wash with PBS;
   add M.O.M. diluent (600 µL of stock in 7500 µL PBS) to the tissues, incubate 5 min at RT;
   aspirate;
   add antibodies (diluted in M.O.M. diluent) to the tissues, incubate 60 min at RT;
   wash with PBS;
   add M.O.M. biotinylated anti-mouse IgG reagent (10 µL stock in 2500 µL M.O.M. diluent) to the tissues, incubate 10 min at RT;
   wash with PBS;
   add Vectastain ABC Elite kit (30 min before use: 2 drops A+2500 µL PBS, mix, add 2 drops B, mix; Vector #PK-6200) to the tissues, incubate 10 min at RT;
   wash with PBS;
   slides 4 min in PBS/0.5% Triton X-100;
   stain in DAB solution;
   wash with PBS;
   put slides 1 min in dest. water;
Counterstaining:
   put slides 1 min in Haematoxylin solution;
   wash in running water;
   put slides 1 sec in HCl/EtOH;
   wash in running water;
   put slides 20 sec in ammonium-water;
   wash in running water;
   put slides in 70% EtOH, 96% EtOH, 100% EtOH abs. (3 times/20 sec each);
   put slides in xylene for 1 min, 2 min, 2 min;
Buffers and Reagents:
Citrate Buffer:
21.01 g citric acid monohydrate in 800 mL dest. water
Adjust pH=6 with 2 M NaOH, then fill with dest. water to 1000 mL
Tris/EDTA Buffer: 0.01 M Tris/0.001 M EDTA; pH=8
HCl/EtOH:
175 mL EtOH abs.
2.5 mL HCl 37%
72.5 mL dest. water
Ammonium water: 250 mL dest. water+10 drops ammonium solution (32%)
Haematoxylin: 160 mL Papanicolaou Solution 1a Harris' Haematoxylin solution, Merck #1.092.530.500+80 mL dest. water (filter before use)!
DAB solution: 125 mg DAB in 250 mL PBS/0.5% Triton X-100, filter and add 25 µL 30% $H_2O_2$ before use
Mouse anti-E-cadherin (Abcam #ab1416; 1:100)
M.O.M. kit basic: Vector #BMK-2202

Example 3

E-Cadherin Expression on Cultured Cells

Figure 1:
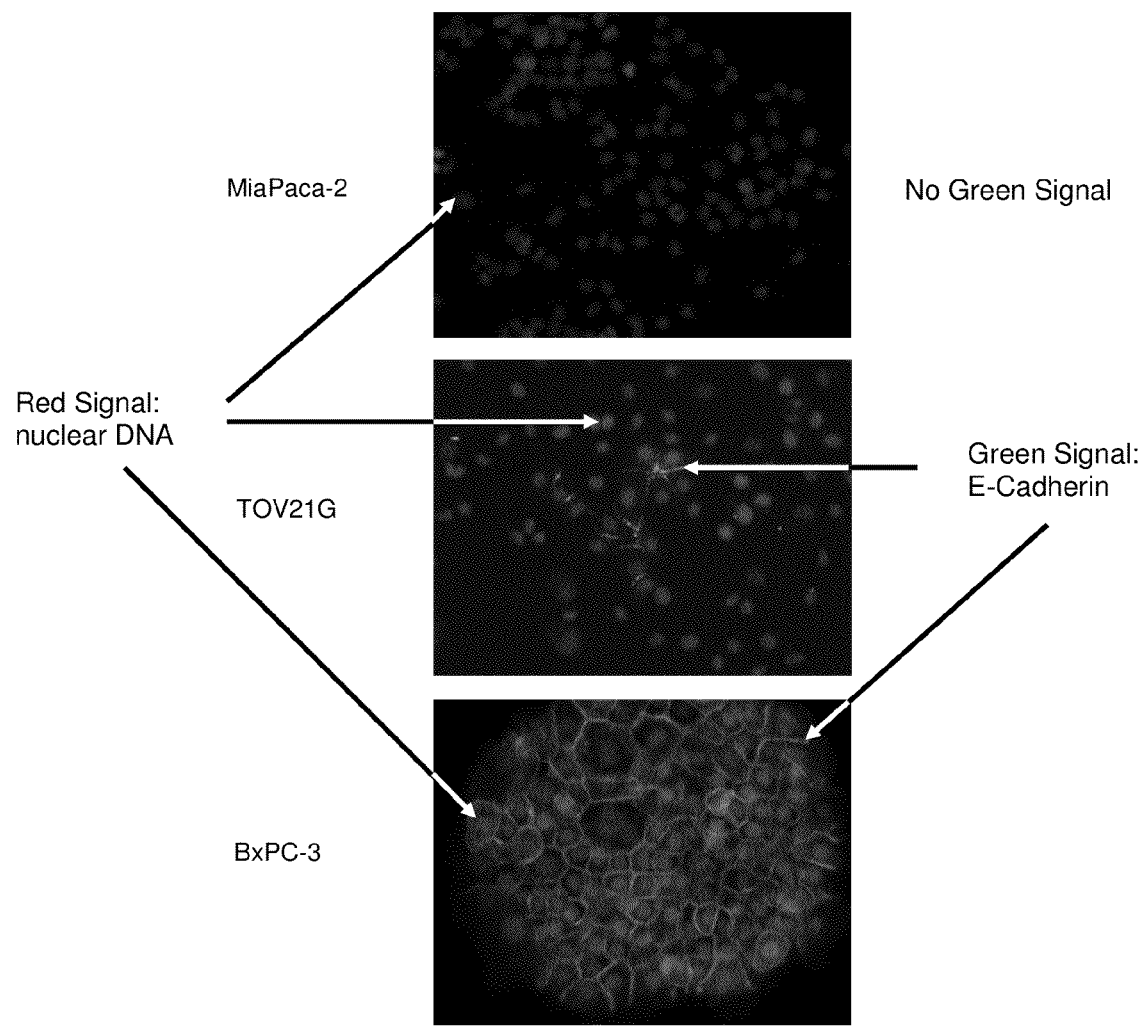
FIG. 1: E-Cadherin Expression on Cultured Cells

Human cancer cells were seeded in chamber slides and stained with specific antibodies against human E-cadherin. Antibody binding was detected with a secondary antibody labeled with fluorescent dye (Alexa 488, green signal). Nuclear DNA was stained with propidium iodide (PI, red signal). E-cadherin was either absent or expressed in a small fraction of cells (see the TOV-21G and MiaPaca2 cell lines). In contrast, BxPC-3 cells displayed an epithelial phenotype with strong membrane expression of E-cadherin in most cells. The results of this experiment are depicted in FIG. 1.

Example 4

Immunofluorescence Protocol for Determining E-Cadherin Expression in Cultured Tumor Cells Grow the selected cell lines in 4 chamber tissue-culture-treated glass slides until near confluency;
   Aspirate the tissue culture medium and fix the slides with acetone/methanol (1:1 v/v) for 10 min at 4° C.;
   Allow the slides to dry at room temperature for 5 min and store at −80° C. until use;
Staining:
   thaw slides for 10 min at RT;
   wash with PBS;
   incubate slides in blocking serum 10% normal goat serum, 20 min at RT;
   aspirate serum and do not wash;
   incubate with the E-cadherin antibody 1:200 in 2% BSA/PBS for 60 min at RT;
   wash with PBS;
   incubate with secondary antibody Alexa 488 conjugated goat anti-mouse (1:1000 in PBS) for 45 min at RT;
   wash with PBS;
   stain for 2 min at RT with 0.5 µg/mL propidium iodide in PBS;
   wash with PBS;
   coverslip with Dako fluorescence mounting medium; store in the dark at 4° C. until microscopic examination;
Buffers and Reagents:
Citrate Buffer:
21.01 g citric acid monohydrate in 800 mL distilled water
Adjust pH=6 with 2 M NaOH, then fill with distilled water to 1000 mL
Mouse anti-human E-cadherin (Abcam #ab1416)
Normal goat serum (Vector Laboratories #S-1000)

Alexa 488 conjugated goat anti-mouse Invitrogen # a-11017
DakoCytomation fluorescence mounting medium # S3023
Propidium Iodide Sigma # P4170

Example 5

Immunohistochemistry Protocol (ABC Method) for Determining E-Cadherin Expression in Human Tissue Samples Deparaffinization:
  heat slides for 1 h at 65° C.;
  put slides in xylene for 3×5 min, then in abs. EtOH, 96% EtOH, 70% EtOH (3×20 sec each);
  wash in distilled water;
Antigen Retrieval:
  put slides in citrate buffer for 20 min in an autoclave at 121° C./1 bar
  allow slides to cool at RT for 30 min;
  wash with PBS;
Staining:
  incubate slides for 5 min in 3% $H_2O_2$ in PBS;
  wash with PBS;
  incubate in blocking serum: 10% normal horse serum (Vector Laboratories #S-2000) in PBS/2% BSA to the tissues, incubate 30 min at RT;
  aspirate serum and do not wash the slides;
  add mouse anti-E-cadherin (Abcam #ab1416; 1:200 in PBS/2% BSA) to the tissues, incubate 60 min at RT;
  wash with PBS;
  add biotinylated horse anti-mouse IgG (Vector Laboratories #BA-2000; 1:200 in PBS) to the tissues, incubate 30 min at RT;
  wash with PBS;
  add Vectastain ABC Standard kit (1:100 in PBS; Vector #PK-4000) to the tissues, incubate 30 min at RT;
  wash with PBS;
  put slides 4 min in PBS/0.5% Triton X-100;
  stain in DAB solution;
  wash with PBS;
  put slides 1 min in distilled water;
Counterstaining:
  stain 1 min in haematoxylin solution;
  wash in running water;
  put slides 1 sec in HCl/EtOH;
  wash in running water;
  put slides 20 sec in ammonium-water;
  wash in running water;
  dehydrate the sections in 70% EtOH, 96% EtOH, abs. EtOH (3 times/20 sec each);
  xylene (×3) for 1 min, 2 min, 2 min;
  coverslip with Entellan;
Buffers and Reagents:
Citrate Buffer:
21.01 g citric acid monohydrate in 800 mL distilled water
Adjust pH=6 with 2 M NaOH, then fill with distilled water to 1000 mL
HCl/EtOH:
175 mL abs. EtOH
2.5 mL HCl 37%
72.5 mL distilled water
Ammonium-Water:
250 mL distilled water+10 drops ammonium solution (32%)
Haematoxylin:
160 mL Papanicolaou Solution la Harris' Haematoxylin solution, Merck #1.092.530.500
80 mL distilled water
filtrate before use!
DAB Solution:
125 mg DAB (Sigma # D5905) in 250 mL PBS/0.5% Triton X-100, filtrate and add 25 µL 30% $H_2O_2$ before use
Normal horse serum (Vector Laboratories #S-2000)
Mouse anti-human E-cadherin (Abcam #ab1416)
Biotinylated horse anti-mouse IgG (Vector Laboratories #BA-2000)
Vectastain ABC Standard kit (1/100 in PBS; Vector #PK-4000)
Entellan (Merk 1.07961.0100)

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, detailed Description, and Examples is hereby incorporated herein by reference.

The invention claimed is:

1. A method of treating a carcinoma of the pancreas or ovarian cancer in a patient, said method comprising the following steps:
   (a) determining whether said patient is susceptible to treatment with a protein tyrosine kinase 2 (PTK2) inhibitor by detecting the amount of expression of the E-cadherin protein in a cancer sample taken from said patient, wherein an E-cadherin protein immunoreactivity score (IRS) of 0 indicates that the patient is susceptible to treatment with a PTK2 inhibitor; and
   (b) treating said patient with a protein tyrosine kinase 2 (PTK2) inhibitor if it has been determined that said patient is susceptible to treatment with a protein tyrosine kinase 2 (PTK2) inhibitor.

2. The method of claim 1, wherein said cancer patient is a mammal.

3. The method of claim 2, wherein said mammal is a human.

4. The method of claim 1, wherein said detection of the expression of the E-cadherin protein in a cancer sample of a cancer patient is conducted by way of an immunohistochemistry (IHC) method.

5. The method of claim 4, wherein said IHC method employs a primary antibody which is specific for E-cadherin and a secondary antibody which specifically reacts with the primary antibody.

* * * * *